(12) United States Patent
Rege et al.

(10) Patent No.: US 10,736,828 B2
(45) Date of Patent: *Aug. 11, 2020

(54) DENTAL STAIN REMOVAL AND PREVENTION

(71) Applicant: Colgate-Palmolive Company, New York, NY (US)

(72) Inventors: Aarti Rege, East Windsor, NJ (US); David Suriano, Edison, NJ (US); Richard Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/143,533

(22) Filed: Sep. 27, 2018

(65) Prior Publication Data

US 2019/0029935 A1 Jan. 31, 2019

Related U.S. Application Data

(63) Continuation of application No. 15/502,255, filed as application No. PCT/US2015/043033 on Jul. 31, 2015, now Pat. No. 10,098,822.

(60) Provisional application No. 62/035,036, filed on Aug. 8, 2014.

(51) Int. Cl.
*A61K 8/27* (2006.01)
*A61Q 11/00* (2006.01)

(52) U.S. Cl.
CPC ............. *A61K 8/27* (2013.01); *A61Q 11/00* (2013.01); *A61K 2800/30* (2013.01); *A61K 2800/92* (2013.01)

(58) Field of Classification Search
CPC .................................... A61K 7/16; A61K 7/18
USPC ..................................................... 424/49, 58
See application file for complete search history.

(56) References Cited

U.S. PATENT DOCUMENTS

| 3,622,662 | A | * | 11/1971 | Roberts | A61K 8/24 424/54 |
|---|---|---|---|---|---|
| 3,746,555 | A | | 7/1973 | Muhler | |
| 5,256,402 | A | | 10/1993 | Prencipe et al. | |
| 6,221,340 | B1 | | 4/2001 | Yu et al. | |
| 6,290,935 | B1 | | 9/2001 | Masters et al. | |
| 6,344,184 | B1 | | 2/2002 | Rolla | A61K 8/27 424/49 |
| 8,628,755 | B2 | * | 1/2014 | Prencipe | A61K 8/24 424/49 |
| 10,154,948 | B2 | | 12/2018 | Vemishetti et al. | |
| 10,172,770 | B2 | | 1/2019 | Rege | |
| 10,179,098 | B2 | | 1/2019 | Rege et al. | |
| 10,258,551 | B2 | | 4/2019 | Rege et al. | |
| 10,278,906 | B2 | | 5/2019 | Rege et al. | |
| 2008/0138298 | A1 | | 6/2008 | Glandorf | A61K 8/27 424/52 |
| 2009/0010970 | A1 | | 1/2009 | Velada | |
| 2009/0214451 | A1 | | 8/2009 | Canham | |
| 2011/0236442 | A1 | * | 9/2011 | Miser | A23G 4/064 424/401 |
| 2012/0045495 | A1 | | 2/2012 | Martinetti et al. | |
| 2015/0305993 | A1 | | 10/2015 | Rege et al. | |
| 2015/0328094 | A1 | | 11/2015 | Xu et al. | |
| 2015/0335552 | A1 | | 11/2015 | Liu et al. | |
| 2017/0367949 | A1 | | 12/2017 | Rege et al. | |
| 2018/0168957 | A1 | | 6/2018 | Rege et al. | |

FOREIGN PATENT DOCUMENTS

| EP | 0040938 | 12/1981 |
|---|---|---|
| WO | WO 2000/47173 A1 | 8/2000 |
| WO | WO 2002/07695 A2 | 1/2002 |
| WO | WO 2006/022848 | 3/2006 |
| WO | WO 2011/117216 | 9/2011 |
| WO | WO 2014/088573 | 6/2014 |
| WO | WO 2014/098828 | 6/2014 |
| WO | WO 2014/100928 | 7/2014 |

OTHER PUBLICATIONS

Datashets.scbt.com, "Zinc phosphate" MSDS sc-251448 Jul. 29, 2010.
International Search Report and Written Opinion in International Application No. PCT/US2015/043033, dated Oct. 30, 2015.
McInerney et al., 1992, "Evaluation of internal sealing ability of three materials," J. Endodontics 18(8):376-378.
Pizzey, et al., "Antimicrobial effects of o-cymen-5-ol and zinc, alone & in combination in simple solutions and toothpaste formulations", International Dental Journal, 61(s3), pp. 33-40, (2011).

* cited by examiner

Primary Examiner — Walter E Webb

(57) ABSTRACT

Provided herein is a method for removing a chemical stain from a dental surface or inhibiting chemical staining of a dental surface, comprising contacting the dental surface with an oral care composition comprising zinc phosphate and an orally acceptable carrier.

8 Claims, No Drawings

DENTAL STAIN REMOVAL AND PREVENTION

BACKGROUND

A tooth is comprised of an inner dentin layer and an outer hard enamel layer that protects the dentin layer. The enamel layer of a tooth is naturally an opaque white or slightly off-white color. The enamel layer can become stained or discolored. The enamel layer of a tooth is composed of hydroxyapatite mineral crystals that create a somewhat porous surface. It is believed that the pores of the enamel layer allow staining agents and discoloring substances to permeate the enamel and discolor the tooth.

Many substances that a person confronts or comes into contact with on a daily basis can "stain" teeth. In particular, foods and fluids such as tea and coffee that one consumes tend to stain one's teeth. These products or substances tend to accumulate on the enamel layer of the tooth and form a pellicle film over the teeth. These staining substances can then permeate the enamel layer. This problem occurs gradually over many years, but imparts a noticeable discoloration of the enamel of one's teeth.

Abrasive agents (for example, silica-based agents) are often used in oral care compositions for stain removal. However, brushing with compositions comprising such agents often leads to enamel damage. This can cause problems such as dentinal hypersensitivity. Peroxide-based agents are also known to have teeth whitening effects. However, peroxide-containing compositions are often unstable and lose whitening efficacy during storage. It is also known to use polyphosphate compounds (for example, pyrophosphates, tripolyphosphates and hexametaphosphates) for stain removal. However, such polyphosphate compounds may interfere with enamel remineralization (i.e. the reformation of crystalline hydroxyapatite—the main constituent of enamel) due to their crystal growth inhibiting properties.

Therefore, it would be desirable to provide further methods of stain removal and prevention which overcome these disadvantages.

BRIEF SUMMARY

The present inventors have unexpectedly found that zinc phosphate is effective in both removing chemical stains from a dental surface and in preventing the deposition of chemical stains on a tooth surface.

Accordingly, in a first aspect, there is provided a method for removing a chemical stain from a dental surface, comprising contacting the dental surface with zinc phosphate, wherein the zinc phosphate is provided in an oral care composition comprising an orally acceptable carrier.

In a second aspect, there is provided a method for inhibiting chemical staining of a dental surface, comprising contacting the dental surface with zinc phosphate, wherein the zinc phosphate is provided in an oral care composition comprising an orally acceptable carrier.

Optionally, after contacting the dental surface with zinc phosphate, the dental surface is exposed to a chemical staining inducing material, wherein a chemical staining resulting from such exposure is inhibited by contact of the dental surface with the oral care composition.

Preferably, the oral care composition comprises zinc phosphate in an amount of from 0.1 weight % to 10 weight % by total of the composition. More preferably, the oral care composition comprises zinc phosphate in an amount of from 0.1 weight % to 8 weight % by total weight of the composition. More preferably, the oral care composition comprises zinc phosphate in an amount of from 0.1 weight % to 5 weight % by total weight of the composition. More preferably, the oral care composition comprises zinc phosphate in an amount of from 0.1 weight % to 3 weight % by total weight of the composition. Most preferably, the oral care composition comprises zinc phosphate in an amount of from 0.1 weight % to 0.5 weight % by total weight of the composition.

Optionally, the oral care composition further comprises one or more agents selected from: surfactants, desensitizing agents, whitening agents, tartar control agents, binders, thickening agents, detergents, adhesion agents, foam modulators, pH modifying agents, mouth feel agents, sweeteners, flavorants, colorants, preservatives, humectants, fluoride sources and combinations thereof.

Optionally, the oral care composition is selected from mouthwashes, sprays, dentifrices, oral strips, chewing gums and lozenges. Preferably, the oral care composition is a dentifrice.

Optionally, contacting the dental surface with the oral care composition comprises rinsing, spraying or brushing the dental surface with the composition, placing the composition on the dental surface, or chewing the composition Optionally, the methods comprise increasing the whiteness of the dental surface. Further optionally, the oral care composition is free of whitening agents other than the zinc phosphate.

Optionally, the chemical staining or the chemical stain is induced by tobacco products, tea and/or coffee.

In a third aspect, there is provided a use of zinc phosphate, in an oral care composition comprising an orally acceptable carrier, for removing a chemical stain from a dental surface, wherein the removal of the chemical stain comprises contacting the dental surface with the oral care composition.

In a fourth aspect, there is provided a use of zinc phosphate, in an oral care composition comprising an orally acceptable carrier, for inhibiting chemical staining of a dental surface, wherein the inhibition of chemical staining comprises contacting the dental surface with the oral care composition.

Optionally, contacting the dental surface with the oral care composition comprises rinsing, spraying or brushing the dental surface with the composition, placing the composition on the dental surface, or chewing the composition.

Optionally, the use comprises increasing the whiteness of the dental surface. Further optionally, the chemical staining or the chemical stain is induced by tobacco products, tea and/or coffee.

The oral care composition and chemical stain may be as defined herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one arrangement, provided herein is a method for removing a chemical stain from a dental surface, comprising contacting the dental surface with an oral care composition comprising zinc phosphate and an orally acceptable carrier.

In another arrangement, provided herein is a method for inhibiting chemical staining of a dental surface, comprising contacting the dental surface with the oral care composition comprising zinc phosphate and an orally acceptable carrier.

A "dental surface" as referred to herein is a surface of a natural tooth or a hard surface of artificial dentition including a crown, cap, filling, bridge, dental implant and the like.

A "chemical stain" as referred to herein is a discoloration of a dental surface which is caused by adsorption or absorption of a colored agent on or into the surface, or caused by chemical reaction of a material of the dental surface (for example, dental enamel) with a colored or non-colored agent contacting the surface. "Chemical staining" as referred to herein is the formation and/or development of a chemical stain.

The methods described herein comprise contacting a dental surface with zinc phosphate and an orally acceptable carrier, as defined above. The methods are applicable to dental surfaces of non-human mammals such as companion animals (for example, dogs and cats), as well as to humans. In one embodiment, the dental surface is a surface of a natural tooth of a mammal, for example a human. The methods described herein are for cosmetic purposes.

Where the dental surface is substantially free of chemical stains, the present methods are effective to inhibit or prevent the formation and development of new chemical stains, as can occur for example by oral use of tobacco products (including smoking) or by drinking tea or coffee, subsequent to treatment according to the present methods. Where the dental surface already possesses some degree of chemical staining, the present methods are effective to inhibit or prevent further development of the existing stain.

Accordingly, in one embodiment, the method defined herein further comprises, after contacting the dental surface with zinc phosphate and an orally acceptable carrier, exposing the dental surface to a chemical stain-inducing material such as a tobacco product, tea or coffee. Chemical staining resulting from such exposure is, in this embodiment, inhibited or prevented by the prior contacting of the dental surface with the zinc phosphate. In some embodiments, the dental surface is substantially free of chemical stains prior to exposing to a chemical stain-inducing material as defined above.

It is desirable that the zinc phosphate should remain in contact with the dental surface for a period of time sufficient to provide effective prevention, inhibition or removal of chemical staining. In one embodiment prevention includes providing a coating that prevents stains from adhering to the dental surface. Depending on various factors including the nature of other materials optionally present in combination with the zinc phosphate, the precise procedure by which contact is effected (e.g., rinsing, brushing, placement of a strip, painting or chewing) and the desired degree and/or duration of inhibition of staining, a suitable minimum period of contact can be from 10 seconds to 8 hours. Where the zinc phosphate is applied as a component of a mouthwash, an illustrative minimum period of rinsing is from 10 seconds to 2 minutes. Where the zinc phosphate is applied as a component of a dentifrice, an illustrative minimum period of brushing is from 30 seconds to 5 minutes, or at least 1 minute, or at least 2 minutes. Where the zinc phosphate is applied as a component of an oral strip, the strip is placed on the dental surface illustratively for a period of from 15 minutes to 8 hours (for example, overnight). Where the zinc phosphate is applied as a component of a liquid whitener composition, the composition is painted onto the dental surface and left in place illustratively for a period of from 5 minutes to 8 hours (for example, overnight). Where the zinc phosphate is applied as a component of a chewing gum, an illustrative minimum period of chewing is from 1 to 20 minutes.

Increasing the degree of agitation in the mouth during rinsing, brushing or chewing can lead to improved contact of the zinc phosphate with the dental surface and enhance the degree of stain prevention or removal. Thus, in an embodiment where the zinc phosphate is present as an ingredient of a dentifrice, vigorous brushing with the dentifrice can be particularly effective.

In some embodiments, the zinc phosphate is applied to the dental surface by means of a dental tray. Accordingly, further provided is a dental tray comprising an oral care composition as defined herein. The dental tray may be formed by procedures that are well-known in the art of oral care. Dental trays are generally formed to correspond to the structure of the dental surface. Typically, the oral are composition comprising zinc phosphate is placed in the tray, and the tray is placed into an oral cavity and against the dental surface to be treated. The tray with the composition during home use may be left in the oral cavity for a period of from 10 minutes to several hours; i.e. up to 12 or more hours. If the treatment is in a dental office, the time of the contact typically will be from 0.5 hours to 2 hours.

Zinc Phosphate

Typically, the zinc phosphate ($Zn_3(PO_4)_2$) is incorporated into the oral care composition as a preformed salt. By "preformed salt" it is meant that the zinc phosphate salt is not formed in situ in the oral care composition (for example, through the reaction of phosphoric acid and zinc ions). In some embodiments, the zinc phosphate salt is a hydrated salt. In other embodiments, the zinc phosphate may be made in situ (for example, through the reaction of phosphoric acid and zinc ions).

In some embodiments, the oral care composition comprises zinc phosphate in an amount of from 0.1 weight % to 10 weight %, or from 1 weight % to 10 weight % by total weight of the composition. In some embodiments, the oral care composition comprises zinc phosphate in an amount of from 1 weight % to 9 weight %, from 1 weight % to 8 weight %, from 1 weight % to 7 weight %, from 1 weight % to 6 weight %, from 1 weight % to 5 weight %, from 1 to 4 weight %, from 1 weight % to 3 weight %, or from 1 weight % to 2 weight % by total weight of the composition. In other embodiments, the oral care composition comprises zinc phosphate in an amount of from 0.5 weight % to 3 weight %, from 0.5 weight % to 2 weight % or from 0.5 weight % to 1 weight % by total weight of the composition. In further embodiments, the oral care composition comprises zinc phosphate in an amount of from 5 weight % to 10 weight % from 5 weight % to 9 weight %, from 5 weight % to 8 weight %, or from 5 weight % to 7 weight % by total weight of the composition. In further embodiments, the oral care composition comprises zinc phosphate in an amount of from 0.5 weight % to 1.5 weight % or from 1 weight % to 1.5 weight %, by total weight of the composition. In still further embodiments, the oral care composition comprises zinc phosphate in an amount of from 0.1 weight % to 1.5 weight %, by total weight of the composition.

In some embodiments, the oral care composition comprises zinc phosphate in an amount of from 0.1 weight % to 5 weight %, or from 0.5 weight % to 3 weight %, by total weight of the composition. In some embodiments, the oral care composition comprises zinc phosphate in an amount of from 0.1 weight % to 4 weight %, from 0.1 weight % to 3 weight %, from 0.1 weight % to 2 weight %, from 0.1 weight % to 1 weight %, or from 0.1 weight % to 0.5 weight %, or from 0.1 to 0.3 weight % by total weight of the composition. In other embodiments, the oral care composition comprises zinc phosphate in an amount of from 0.5 weight % to 2 weight % or from 0.5 weight % to 1 weight % by total weight of the composition. In further embodiments, the oral care composition comprises zinc phosphate in an amount of from 0.5 weight % to 1.5 weight % or from 1 weight % to 1.5 weight %, by total weight of the composition. In still further embodiments, the oral care composition comprises zinc phosphate in an amount of from 0.1 weight % to 1.5 weight %, by total weight of the composition.

Form of Composition

A composition useful in practicing the methods of the present invention can be, for example, a mouthwash, a spray, a dentifrice, a gel, an oral strip, a liquid whitener, a chewing gum, a bead, a chew, a lozenge or a composition which is applied to the teeth using a dental tray. A dentifrice includes, without limitation, a toothpaste, gel and powder. A "liquid whitener" herein encompasses semi-liquid compositions such as gels as well as flowable liquids, which may be applied to a dental surface by painting with a brush or other suitable device. "Painting" herein means application of a thin layer of the composition to the dental surface.

Carriers and Other Ingredients

The expression "orally acceptable carrier" as used herein denotes any safe and acceptable materials for oral use. Such materials include water or other solvents that may contain a humectant such as glycerin, sorbitol, xylitol and the like. In some aspects, the term "orally acceptable carrier" encompasses all of the components of the oral care composition except for the zinc phosphate. In other aspects, the term refers to inert or inactive ingredients that serve to deliver the zinc phosphate, and/or any other functional ingredients, to the oral cavity.

Orally acceptable carriers for use in the invention include conventional and known carriers used in making mouthwashes or mouthrinses, toothpastes, tooth gels, tooth powder, lozenges, gums, beads, edible strips, tablets and the like. Carriers should be selected for compatibility with each other and with other ingredients of the composition.

The following non-limiting examples are provided. In a toothpaste composition, the carrier is typically a water/humectant system that provides a major fraction by weight of the composition. Alternatively, the carrier component of a toothpaste composition may comprise water, one or more humectants, and other functional components other than the zinc phosphate. In a mouthrinse or a mouthwash formulation, the carrier is typically a water/alcohol liquid mixture in which the zinc phosphate is dissolved or dispersed. A mouthrinse or a mouthwash formulation may further comprise an amino acid or a betaine surfactant to enhance the solubility of the zinc phosphate. In a dissolvable lozenge, the carrier typically comprises a solid matrix material that dissolves slowly in the oral cavity. In chewing gums, the carrier typically comprises a gum base, while in an edible strip, the carrier typically comprises one or more film forming polymers.

The compositions used in the methods provided herein may comprise one or more additional oral care ingredients which may have specific functions. The one or more additional oral care ingredients may optionally be selected from the group consisting of: surfactants, desensitizing agents, whitening agents, tartar control agents, binders, thickeners, detergents, adhesion agents, foam modulators, pH modifying agents, mouth feel agents, sweeteners, flavourants, colorants, preservatives, humectants, fluoride sources and combinations thereof.

Surfactants may be present in the oral care compositions used in the methods provided herein to provide foaming, taste, flavour, texture and mouth feel properties to the compositions, and in particular to render the compositions more cosmetically acceptable. Suitable surfactants include, without limitation, water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine. Preferably, the surfactant comprises sodium lauryl sulfate (SLS).

The compositions used in the methods provided herein optionally incorporate one or more desensitizing agents. These include, without limitation, potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 weight % to about 20 weight % by total weight of the composition, depending on the agent chosen. The compositions used in the methods defined herein may also be used to treat hypersensitivity by blocking dentin tubules when applied to a tooth surface.

The compositions used in the methods provided herein may optionally include a tooth whitening or tooth bleaching agent. Suitable whitening and bleaching agents include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be incorporated in effective amounts, for example, from 1 weight % to 20 weight % by total weight of the composition, depending on the agent chosen.

In some embodiments, the compositions used in the methods provided herein are free of whitening or tooth bleaching agents. The present inventors have found that zinc phosphate provides a whitening effect when applied to a dental surface, thus obviating the need for further whitening or bleaching agents.

The whitening effects of a composition may be quantified using a measurement of the L*a*b* color space. (L*a*b* refers to stain score in accordance with the Commission International de L'Eclairage Laboratory (CIELAB) color scale. L* represents lightness/darkness, a* represents red-green chroma, and b* represents yellow-blue chroma). From measurement of the L*a*b* values, a whitening index $\Delta W^*$ can be calculated: $\Delta W^* = W^*\text{final} - W^*\text{initial}$, where $W^* = (a^{*2} + b^{*2} + (L^* - 100)^2)^{1/2}$. L*a*b* values can be measured using an optic shade-taking system to analyse and identify the color of a substrate (or dental surface).

The compositions used in the methods defined herein may optionally include tartar control agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate, long chain polyphosphates such as sodium hexametaphosphate and cyclic phosphates such as sodium trimetaphosphate.

The compositions used in the methods defined herein may further comprise a binder. Any conventional binder may be utilized. Suitable binding agents include marine colloids; carboxyvinyl polymers; carrageenans; starches; cellulosic polymers such as hydroxyethylcellulose, carboxymethylcellulose (carmellose), hydroxypropyl methyl cellulose, and salts thereof (e.g., carmellose sodium); natural gums such as karaya, xanthan, gum arabic and tragacanth; chitosan; colloidal magnesium aluminum silicate; and colloidal silica. Preferably, a binder is present in the composition in an amount from 0.5 weight % to 5 weight % by total weight of the composition.

Thickening agents which may be incorporated into the compositions used in the methods defined herein include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds and colloidal silica compounds available under the trade designation Cab-o-sil manufactured by Cabot Corporation. Other inorganic thickening agents include natural and synthetic clays such as hectorite clays, lithium magnesium silicate (laponite) and magnesium aluminum silicate (Veegum).

The compositions used in the methods defined herein may optionally comprise one or more adhesion agents. The adhesion agent may by a polymeric adherent material. The polymeric adherent material may be any agent that attaches to the surface of a mammalian tooth and/or to a heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), and carboxymethyl cellulose (CMC). Preferably, the polymeric adherent material comprises at least one cellulose material, for example sodium carboxymethyl cellulose.

The polymeric adherent material may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In one embodiment, a copolymer comprises (PVM/MA). Optionally, the copolymer may be selected from the group consisting of: poly (methylvinylether/maleic anhydride), or poly (methylvinylether/maleic acid), or poly (methylvinylether/maleic acid) half esters, or poly (methylvinylether/maleic acid) mixed salts.

Polymers of any molecular weight may be used, including, for example molecular weights of 50,000 to 500,000 Da, 500,000 to 2,500,000 Da or 2,500,000 to 10,000,000 Da (calculated by either number average or weight average).

The oral care compositions used in the methods defined herein also may include a foam modulator. Foam modulators typically increase the amount of foam produced, for example, when the oral cavity is brushed using the composition in accordance with the methods defined herein. Illustrative examples of foam modulators that increase the amount of foam include, but are not limited to polyoxyethylene and certain polymers including alginate polymers.

The foaming agent is preferably in the oral care composition in an amount from 0.01 to about 0.9 weight %, or from 0.05 to 0.5 weight %, or from 0.1 to about 0.2 weight % by total weight of the composition.

Polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of from 200,000 to 7,000,000 Da, and preferably from 600,000 to 2,000,000 Da, and more preferably from 800,000 to 1,000,000 Da. Polyox® is the trade name for the high molecular weight polyoxyethylene produced by Union Carbide.

Preferably, the compositions used in the methods of the present invention further comprise at least one pH modifying agent. Such agents include acidifying agents to lower pH, basifying agents to raise pH, and buffering agents to control pH within a desired range. The pH modifying agent preferably comprises a basifying agent and/or a buffering agent. For example, one or more compounds selected from acidifying, basifying and buffering agents can be included to provide a pH of 2 to 10, or in various illustrative embodiments, a pH of 2 to 8, 3 to 9, 4 to 8, 5 to 7, 6 to 10, or 7 to 9. Any orally acceptable pH modifying agent can be used including, without limitation, carboxylic, phosphoric and sulfonic acids, acid salts (e.g., monosodium citrate, disodium citrate, monosodium malate); alkali metal hydroxides such as sodium hydroxide; carbonates such as sodium carbonate, bicarbonates, and sesquicarbonates; borates; silicates; phosphates (e.g., monosodium phosphate, trisodium phosphate, pyrophosphate salts), imidazole and the like. One or more pH modifying agents are preferably present in a total amount effective to maintain the composition in an orally acceptable pH range.

Mouth-feel agents that may be incorporated into the compositions used in the methods defined herein include materials which impart a desirable texture or other feeling during use of the composition. Such agents include bicarbonate salts, which may impart a "clean feel" to teeth and gums due to effervescence and release of carbon dioxide. Any orally acceptable bicarbonate can be used, including, without limitation, alkali metal bicarbonates such as sodium and potassium bicarbonates, ammonium bicarbonate, and mixtures thereof. One or more bicarbonate salts are optionally present in a total amount of from 0.1 weight % to 50 weight %, for example from 1% to 20 weight %, by total weight of the composition.

The compositions used in the methods defined herein may optionally comprise a sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol. These may be present in an amount of up to 0.5 weight %, optionally from 0.005 weight % to 0.1 weight %, based on the total weight of the composition.

The compositions used in the methods defined herein may optionally comprise a flavorant. Flavorants that may be used in the compositions of the present invention include essential oils as well as various flavoring aldehydes, esters, alcohols, and similar materials. Examples of the essential oils include oils of spearmint, peppermint, aniseed, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The flavourant may be incorporated in the composition in an amount of from 0.1 weight % to 5 weight %, or from 0.5 weight % to 1.5 weight %, by total weight of the composition.

The compositions used in the methods defined herein may comprise at least one colorant. Colorants herein include pigments, dyes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from 0.001 weight % to about 20 weight %, for example, from 0.01 weight % to 10 weight %, or from 0.1 weight % to 5 weight %, by total weight of the composition.

Preservatives, such as chlorhexidine, triclosan, quaternary ammonium compounds (such as benzalkonium chloride) or parabens (such as methyl or propyl paraben) may be incorporated in the compositions used in the methods of the present invention. The amount of preservative is typically up to 0.5 weight %, optionally from 0.05 to 0.1 weight %, by total weight of the composition.

The compositions used in the methods of the present invention may optionally comprise a humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount in the range of from 1 weight % to 70 weight %, for example, from 1 weight % to about 50 weight %, from 2 weight % to 25 weight %, or from 5 weight % to 15 weight %, by total weight of the composition.

Preferably, the compositions used in the methods defined herein comprise a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-Nionic,N,N'-tris(2-ethanol)-dihydrofluoride), ammonium fluoride, and combinations thereof. Optionally, the fluoride ion source includes stannous fluoride, sodium fluoride, amine fluorides, sodium monofluorophosphate, as well as mixtures thereof. Preferably, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions used in the invention in an amount of from 0.001 weight % to 10 weight %, e.g., from 0.003 weight % to 5 weight %, or from 0.01 weight % to 1 weight % or to 0.05 weight %. However, it is to be understood that the weights of fluoride salts to provide the appropriate level of fluoride ion will vary based on the weight of the counter ion in the salt, and one of skill in the art may readily determine such amounts. A preferred fluoride salt may be sodium fluoride.

In a preferred embodiment, the oral care composition comprise from 1 to 3 weight % polyethylene glycol, 1 to 3 weight % cellulosic binder, 0.1 to 0.3 weight % sweetener, 1 to 3 weight % tartar control agent, 20 to 50 weight % humectant, 15 to 20 weight % silica abrasive, 2 to 6 weight % anionic surfactant, 1 to 3 weight % amphoteric surfactant, 0.5 to 2 weight % thickener, and 1 to 3 weight % zinc phosphate, and water (qs).

Uses

The present inventors have unexpectedly found that zinc phosphate is effective in both removing chemical stains from a dental surface and in inhibiting or preventing the formation of chemical stains on a dental surface.

Accordingly, in one arrangement, the present invention provides a use of zinc phosphate, in an oral care composition comprising an orally acceptable carrier, for removing a chemical stain from a dental surface, wherein the removal of the chemical stain comprises contacting the dental surface with the oral care composition.

In another arrangement, the present invention provides a use of zinc phosphate, in an oral care composition comprising an orally acceptable carrier, for preventing or inhibiting chemical staining of a dental surface, wherein the prevention or inhibition of chemical staining comprises contacting the dental surface with the oral care composition.

The oral care composition, chemical staining and prevention or inhibition thereof, and methods of contacting the dental surface are in preferred embodiments, as described herein.

The compositions described herein are accordingly effective as tooth whitening compositions. A tooth whitening composition is a composition which is capable of reducing the discoloration of teeth. A tooth whitening composition may restore the natural color of teeth. Optionally, a tooth whitening composition may reduce or eliminate stains. Multiple applications of a tooth whitening composition may be needed to produce a discernible effect. Preferably, the tooth whitening effect is discernible after the first use of the composition.

Zinc phosphate may advantageously be used over other known stain removal or whitening agents in oral care compositions. Zinc phosphate poses less risk of enamel damage compared to abrasive agents having stain removal properties (for example, silica-based agents). Furthermore, unlike polyphosphate compounds which are known to have stain removal properties, zinc phosphate does not inhibit the recrystallization of hydroxyapatite, the major constituent of enamel. On the contrary, zinc phosphate has been found to have protective effects on the enamel surface, and thus concomitantly provides anti-erosive effects and stain removal/stain prevention effects. Thus, in some arrangements, the methods and uses defined herein further comprise contacting a dental surface with zinc phosphate to prevent or treat enamel erosion (in addition to removing, preventing or inhibiting chemical staining). Furthermore, zinc phosphate may be used in lower concentrations than other abrasives or polyphosphate compounds to achieve stain removal and stain prevention effects. In some embodiments, the oral care compositions as defined herein may comprise a combination of zinc phosphate and an abrasive (for example, a silica-based abrasive) to maximize whitening efficacy.

The following examples illustrate compositions of the invention and their uses. The exemplified compositions are illustrative and do not limit the scope of the invention.

EXAMPLES

Example 1—Dentifrice Composition

Dentifrice compositions were produced according to the present invention, as illustrated in Table 1.

TABLE 1

| dentifrice composition of the present invention | |
|---|---|
| Ingredient | Amount (weight %) |
| Polyethylene glycol | 1 to 3 |
| Cellulosic binder | 1 to 3 |
| Sweetener | 0.1 to 0.3 |
| Tartar control agent (e.g. pyrophosphate salt) | 1 to 3 |
| Humectant | 20 to 50 |
| Silica abrasive | 15 to 20 |
| Anionic surfactant (e.g. alkyl ether sulfate) | 2 to 6 |
| Amphoteric surfactant (e.g. betaine surfactant) | 1 to 3 |
| Thickener | 0.5 to 2 |
| Other minors (e.g. colors, flavors and preservatives) | 1 to 3 |
| Zinc phosphate | 1 to 3 |
| Purified Water | Q.S. |

Example 2—Effect of Zinc Phosphate on Stain Removal

Hydroxyapatite (HAP) disks were stained with coffee prior to applying either a toothpaste comprising 1% zinc phosphate (as illustrated in Table 1) or a toothpaste comprising fluoride silica (control). Stain intensity before and after treatment was quantified using a colorimeter which measured the L*a*b* color space. (L*a*b* refers to a stain score in accordance with the Commission International de L'Eclairage Laboratory (CIELAB) color scale: L* represents lightness/darkness, a* represents red-green chroma, and b* represents yellow-blue chroma). The L value was used to assess stain intensity. The results are illustrated in Table 2.

TABLE 2

| results of stain removal test | | | | | |
|---|---|---|---|---|---|
| Product | | L: Coffee Stain | L: after treatment | ΔL | % ΔL (% relative to stained disk) |
| Zinc phosphate | Run 1 | 78.76 | 85.94 | 7.18 | 9.12 |
| | Run 2 | 79.46 | 85.04 | 5.58 | 7.02 |
| | Run 3 | 78.18 | 87.32 | 9.14 | 11.69 |
| | Run 4 | 79.25 | 87.07 | 7.82 | 9.87 |

TABLE 2-continued

| results of stain removal test | | | | | |
|---|---|---|---|---|---|
| Product | | L: Coffee Stain | L: after treatment | ΔL | % ΔL (% relative to stained disk) |
| | Run 5 | 73.58 | 87.94 | 14.36 | 19.51 |
| | Mean | 77.85 | 86.66 | 8.82 | 11.44 |
| | SD | 2.44 | 1.16 | 3.35 | 4.81 |
| Fluoride silica | Run 1 | 71.12 | 71.97 | 0.85 | 1.2 |
| | Run 2 | 79.80 | 79.66 | −0.14 | −0.17 |
| | Run 3 | 82.65 | 82.39 | −0.26 | −0.31 |
| | Run 4 | 75.02 | 74.14 | −0.88 | −1.17 |
| | Run 5 | 81.39 | 81.25 | −0.14 | −0.17 |
| | Mean | 78.00 | 77.88 | −0.11 | −0.12 |
| | SD | 4.81 | 4.58 | 0.62 | 0.85 |

It can be seen from Table 2 that the toothpaste containing zinc phosphate was very effective in increasing the "lightness" of the HAP disks, indicating increased stain removal. In contrast, the toothpaste containing fluoride silica had a negligible effect on stain removal.

Example 3—Effect of Zinc Phosphate on Stain Prevention

HAP disks were treated with the toothpaste comprising 1% zinc phosphate, or left untreated, prior to staining with coffee. Stain intensity was measured as described in Example 2. The results are illustrated in Table 3.

TABLE 3

| results of stain prevention test | | |
|---|---|---|
| Product | | L (after coffee stain) |
| Zinc phosphate | Run 1 | 89.82 |
| | Run 2 | 89.75 |
| | Run 3 | 90.25 |
| | Run 4 | 89.92 |
| | Run 5 | 88.50 |
| | Mean | 89.65 |
| | SD | 0.67 |
| Untreated | Run 1 | 66.82 |
| | Run 2 | 69.83 |
| | Run 3 | 72.50 |
| | Run 4 | 72.89 |
| | Run 5 | 68.90 |
| | Mean | 70.12 |
| | SD | 2.54 |

As can be seen from Table 3, disks pre-treated with zinc phosphate were significantly more resistant to staining, as compared to untreated disks.

Example 4—Effect of Zinc Phosphate on Stain Prevention (Dose-Dependency)

HAP disks were treated with a toothpaste comprising various concentrations of zinc phosphate (ranging from 0% to 5%), prior to staining with coffee. Stain intensity was measured as described in Example 2. The results are illustrated in Table 4. Delta L values represent the change in L that is observed on staining with coffee. (Coffee staining will decrease lightness of the disks and thus the L value. The smaller the decrease in L, the more effective the stain prevention).

TABLE 4

| Stain prevention - dose dependency | |
|---|---|
| Product | Delta L |
| 0% zinc phosphate | 5.38 |
| 0.5% zinc phosphate | 3.53 |
| 1% zinc phosphate | 2.85 |
| 5% zinc phosphate | 2.23 |

It can be seen from Table 4 that zinc phosphate is effective in preventing dental stains, in a dose-dependent manner. A concentration of zinc phosphate as low as 0.5% is effective.

Whilst particular embodiments of the invention have been illustrated and described, it will be obvious to those skilled in the art that various changes and modifications may be made without departing from the scope of the invention as defined in the appended claims.

What is claimed is:

1. A method for inhibiting chemical staining of a dental surface, comprising contacting the dental surface of a person in need of dental stain reduction, with zinc phosphate, wherein the zinc phosphate is provided in an oral care composition comprising an orally acceptable carrier, wherein after contacting the dental surface with zinc phosphate, the dental surface is exposed to a chemical staining inducing material, and wherein a chemical staining resulting from such exposure is inhibited by contact of the dental surface with the zinc phosphate; and
wherein the zinc phosphate is in an amount from 0.5 weight % to 2 weight %, by total weight of the composition, and wherein the chemical staining or the chemical stain is induced by tobacco products, tea and/or coffee.

2. The method according to claim 1, wherein the oral care composition comprises zinc phosphate in an amount of from 0.5 weight % to 1.5 weight % by total weight of the composition.

3. The method according to claim 1, wherein the oral care composition further comprises one or more agents selected from: surfactants, desensitizing agents, whitening agents, tartar control agents, binders, thickening agents, detergents, adhesion agents, foam modulators, pH modifying agents, mouth feel agents, sweeteners, flavorants, colorants, preservatives, humectants, fluoride sources and combinations thereof.

4. The method according to claim 1, wherein the oral care composition is selected from mouthwashes, sprays, dentifrices, oral strips, chewing gums and lozenges.

5. The method according to claim 4, wherein the oral care composition is a dentifrice.

6. The method according to claim 1, wherein contacting the dental surface with zinc phosphate comprises rinsing, spraying or brushing the dental surface with the oral care composition comprising zinc phosphate, placing the composition on the dental surface, chewing the composition, or placing the composition in a dental tray and placing the tray so as to contact the dental surface.

7. The method according to claim 1, wherein the oral care composition is free of whitening agents other than the zinc phosphate.

8. The method according to claim 1, which comprises increasing the whiteness of the dental surface.

* * * * *